US00PP20459P3

(12) United States Plant Patent
Ackerman et al.

(10) Patent No.: US PP20,459 P3
(45) Date of Patent: Nov. 10, 2009

(54) RASPBERRY PLANT NAMED 'GRANDEUR'

(50) Latin Name: *Rubus idaeus*
Varietal Denomination: GRANDEUR

(75) Inventors: Stephen M. Ackerman, Salinas, CA (US); Scott W. Adams, Watsonville, CA (US)

(73) Assignees: Plant Sciences, Inc., Watsonville, CA (US); Berry R&D, Inc., Watsonville, CA (US)

( * ) Notice: Subject to any disclaimer, the term of this patent is extended or adjusted under 35 U.S.C. 154(b) by 2 days.

(21) Appl. No.: 12/218,464

(22) Filed: Jul. 15, 2008

(65) Prior Publication Data

US 2009/0158480 P1 Jun. 18, 2009

Related U.S. Application Data

(60) Provisional application No. 60/996,988, filed on Dec. 13, 2007.

(51) Int. Cl.
*A01H 5/00* (2006.01)

(52) U.S. Cl. ..... Plt./204

(58) Field of Classification Search ..... Plt./204
See application file for complete search history.

*Primary Examiner*—June Hwu
(74) *Attorney, Agent, or Firm*—Foley & Lardner LLP

(57) ABSTRACT

This invention relates to a new and distinct everbearing variety of raspberry plant named 'GRANDEUR'. The new variety is primarily adapted to the growing conditions of the central coast of California and is characterized by the following: large, firm, light-red fruit of conic shape, even color, and very good flavor. Foliage is slightly concave to slightly convex, medium green; possessing very strong rugosity, and always 3-foliate. Primocanes have an absent to very weak waxy coat, medium thorn density, and medium anthocyanin coloration.

4 Drawing Sheets

Latin name of the genus and species of the plant claimed: *Rubus idaeus.*

Variety denomination: 'GRANDEUR'.

BACKGROUND OF THE INVENTION

The present invention relates to a new and distinct fall bearing raspberry variety designated as 'GRANDEUR'. This new variety is a result of a controlled cross made in 2001 between raspberry variety 'PSI-737' (patented, U.S. Plant Pat. No. 8,639) and raspberry variety 'PS-1509' (unpatented) in an ongoing breeding program. It is unknown as to which parent variety is the seed parent and which parent variety is the pollen parent. The variety is botanically known as *Rubus idaeus.*

The seedling resulting from the aforementioned cross was asexually propagated by dormant canes in Santa Cruz County, Calif. and was subsequently selected by the inventor from a controlled breeding plot in Watsonville, Calif. in 2003. After its selection, the new variety was further asexually propagated by dormant canes, roots and non-dormant root shoot cuttings in Santa Cruz County, Calif., San Joaquin County, Calif. and Siskiyou County, Calif. The new variety was then extensively tested over the next several years in fruiting fields in Santa Cruz County, Calif. This propagation has demonstrated that the combination of traits disclosed herein as characterizing the new variety are fixed and remain true to type through successive generations of asexual reproduction.

BRIEF SUMMARY OF THE INVENTION

'GRANDEUR' is primarily adapted to the climate and growing conditions of the central coast of California. This region provides the necessary year-round temperatures required for it to produce and maintain a strong vigorous plant and to remain in fruit production from July through December on primocanes and in the ensuing year from May through July on the floricanes.

The following traits have been repeatedly observed and are determined to be unique characteristics of 'GRANDEUR', which in combination distinguish this raspberry plant as a new and distinct variety:

1. large fruit size;
2. high fruit firmness;
3. light fruit color;
4. primocane glaucosity ranging from absent to very weak; and
5. light brown floricane color.

The new raspberry variety 'GRANDEUR' differs from 'PSI-737' in mature fruit color. 'PSI-737' has a golden mature fruit color while the new cultivar has red mature fruit color. 'PS-1509' is no longer available for comparison.

The raspberry varieties that are believed to be most closely related to the new raspberry variety 'GRANDEUR' are the raspberry variety 'PS-1049' (patented, U.S. Plant Pat. No. 10,142), and the raspberry variety 'PS-1703' (patented, U.S. Plant Pat. No. 15,151). In comparison to the similar raspberry varieties 'PS-1049' and 'PS-1703', 'GRANDEUR' differs by the following combination of characteristics described in Table 1:

TABLE 1

| Characteristic | 'GRANDEUR' | 'PS-1049' (US PP10,142) | 'PS-1703' (US PP15,151) |
|---|---|---|---|
| 1. Primocane waxy coat (glaucosity) | Ranges from absent to very weak | Strong | Ranges from medium to strong |
| 2. Predominate number of leaflets | Always 3 | Equal 3-5 | Mostly 5 |
| 3. Leaf color (upper side) | 7.5GY 3/4 to 3/6 | 7.5GY 3/4 to 4/4 | 7.5GY 2/4 to 3/4 |
| 4. Leaf shape (cross section) | Ranges from slightly concave to slightly convex | Slightly concave | Ranges from slightly concave to slightly convex |
| 5. Rugosity | Very strong | Medium | Medium to strong |
| 6. Color mature fruit | 5R 4/12 to 3/10 Light to medium red | 5R 3/6 to 3/8 Medium red | 5R 3/10 to 3/8 Medium red |
| 7. Primocane fruit weight (g) | 3.5 | 2.7 | 3.0 |
| 8. Floricane fruit weight (g) | 3.6 | 2.5 | 2.7 |
| 9. Primocane color | 10Y 7/4 to 7/6 Medium green yellow | 5GY 7/4 to 6/4 Light green yellow | 7.5GY 6/2 to 6/4 Medium green yellow |
| 10. Floricane color | 10YR 4/8 to 5/8 Brown | 5YR 4/4 to 4/6 Brown | 7.5YR 4/6 to 4/8 Brown |

For identification, a series of AFLP molecular markers have been determined for this new variety.

BRIEF DESCRIPTIONS OF THE PHOTOGRAPHS

The accompanying color photographs illustrate the overall appearance of typical specimens of the new raspberry variety, 'GRANDEUR' at various stages of development as true as reasonably possible with color reproductions of this type. Color in the photographs may differ slightly from the color value cited in the detailed botanical description which accurately describes the color of 'GRANDEUR'. The depicted plant and plant parts of the new raspberry variety 'GRANDEUR' were taken in Watsonville, Calif. and are approximately 2 to 16 months old:

FIG. 1. shows typical primocane foliage and fruit color; foliate and rugosity characteristics of 'GRANDEUR' taken in the month of September 2007.

DETAILED BOTANICAL DESCRIPTION

Figure 1:
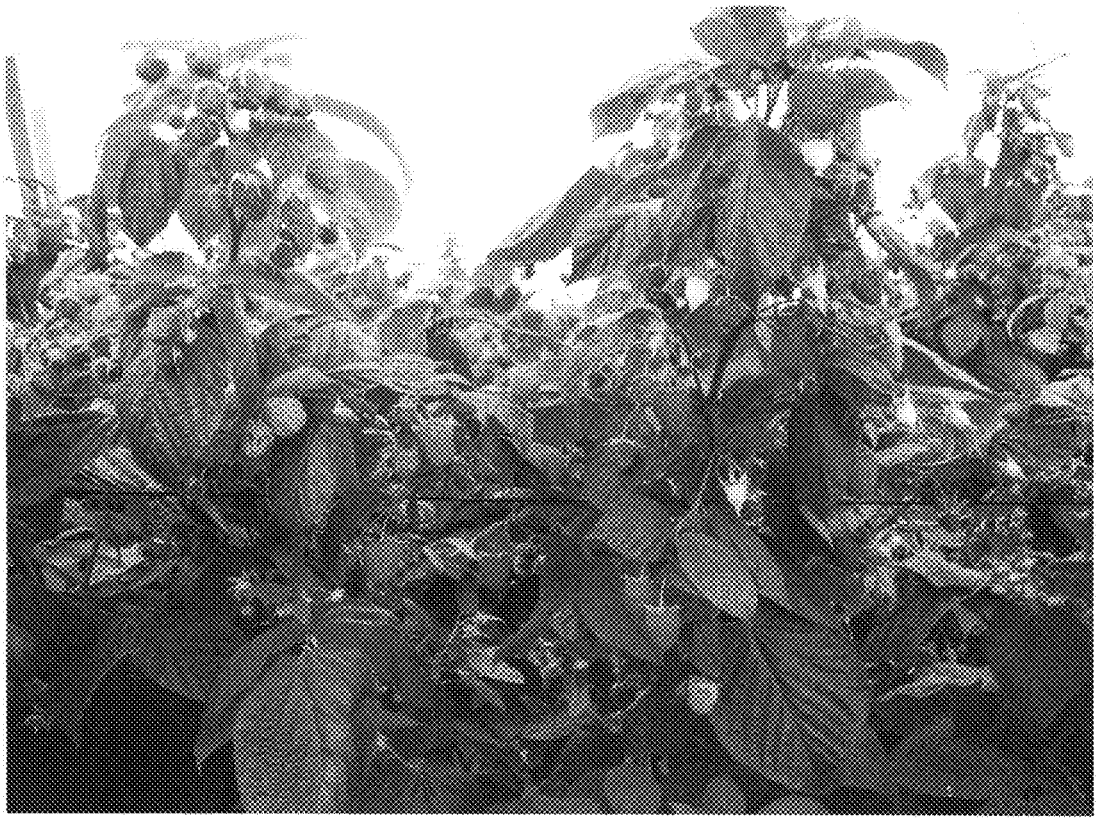
Figure 2:
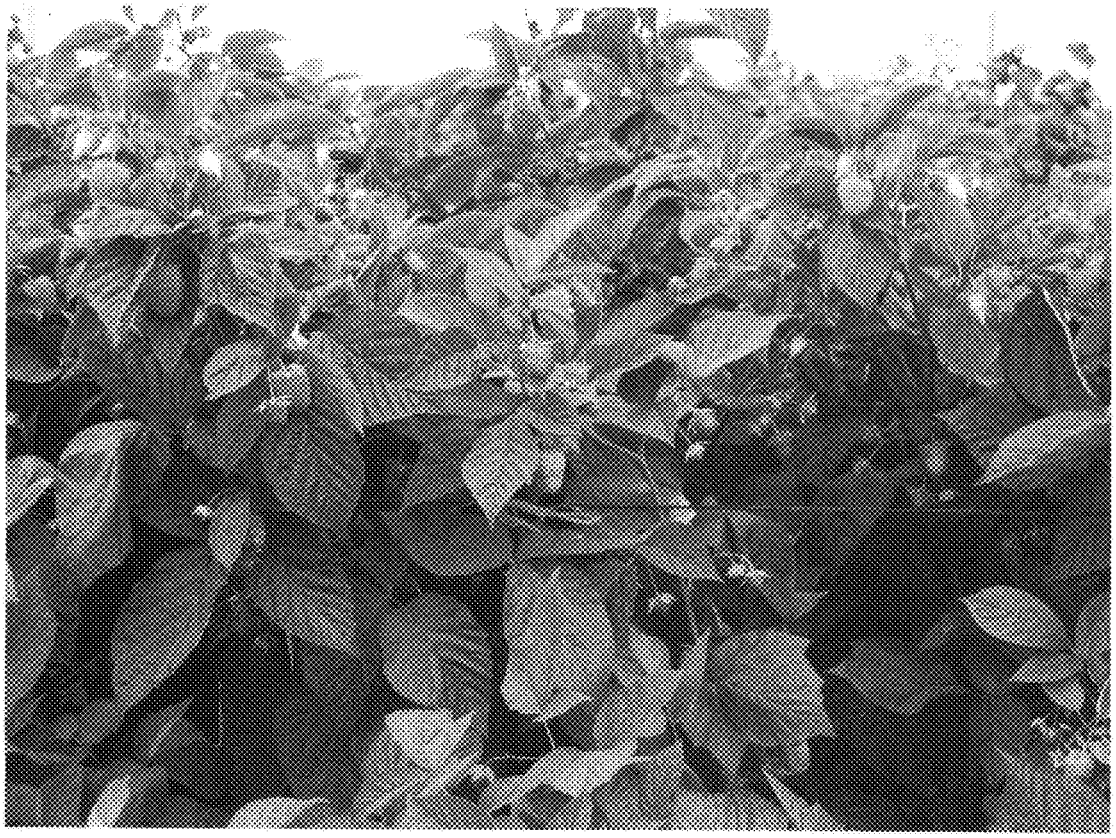
FIG. 2 shows typical floricane foliage and fruit color; foliate and rugosity characteristics of 'GRANDEUR' taken in the month of May 2008.
Figure 3:
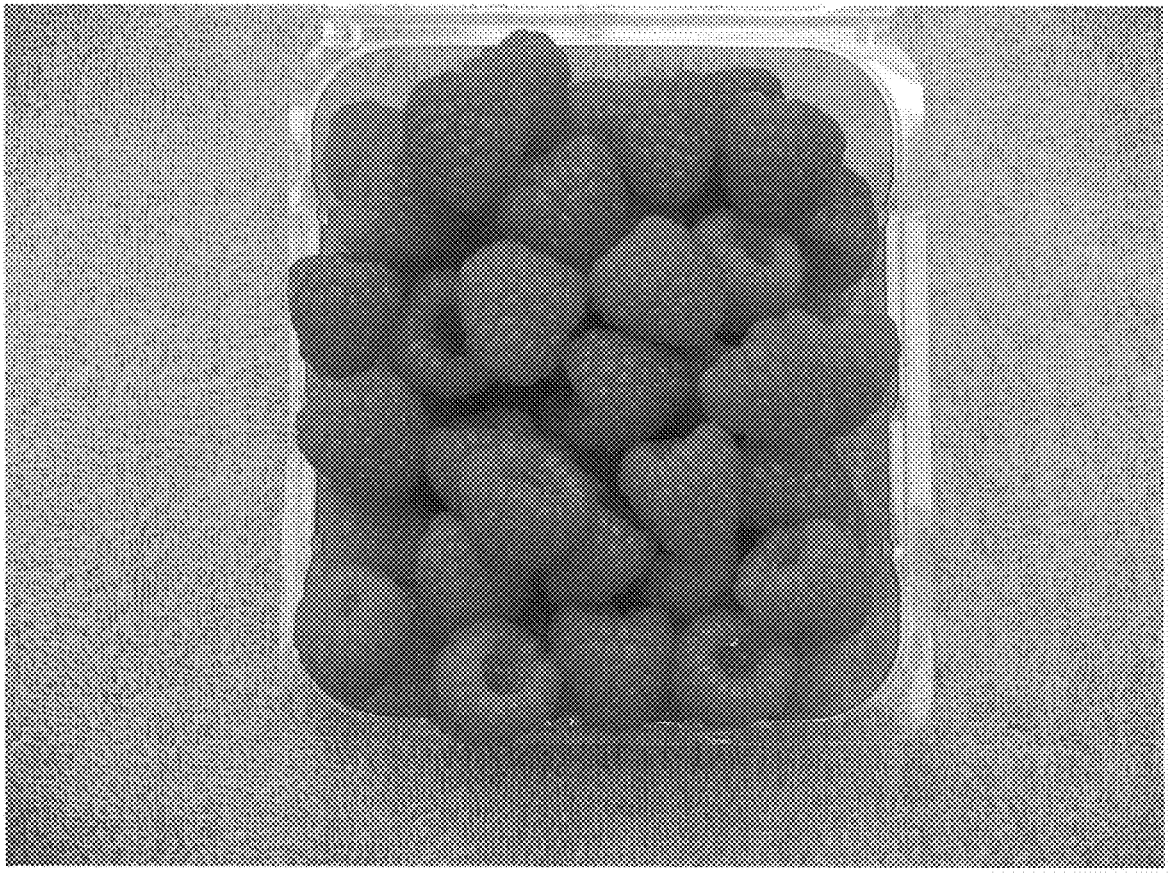
FIG. 3 shows typical harvested fruit of 'GRANDEUR' taken in the month of September 2007.
Figure 4:
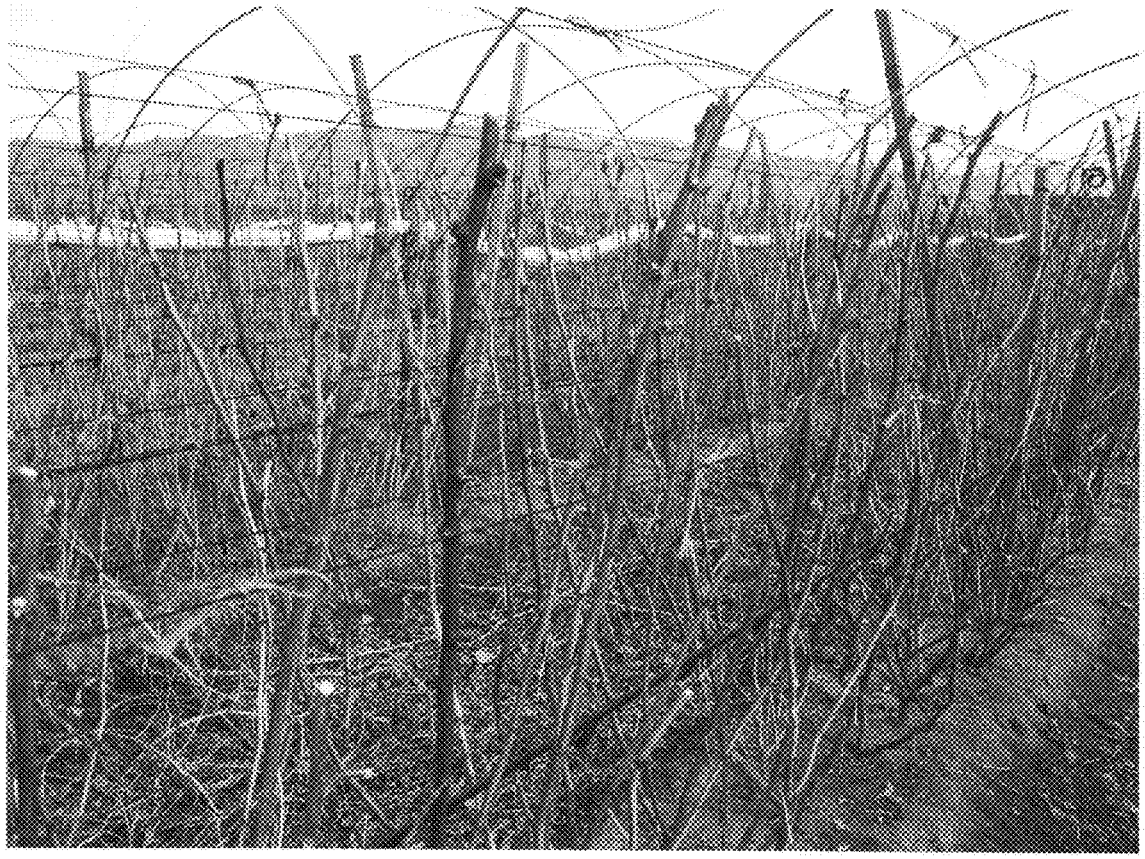
FIG. 4 shows typical dormant cane color characteristics of 'GRANDEUR' taken in the month of February 2007.

'GRANDEUR' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'GRANDEUR', unless otherwise noted, are based upon observations taken during the 2007–2008 growing season in Watsonville, Calif. Primocane measurements and ratings were taken from plants of 'GRANDEUR' dug from a nursery located in San Joaquin County, Calif. during the middle of December 2006 and planted approximately 3 to 4 weeks later in Watsonville, Calif. The approximate age of the observed primocane plants is 7 to 8 months. Floricane measurements and ratings were taken from the same planting of 'GRANDEUR' at an approximate age of 16 to 18 months. Yield observations and fruit quality characteristics are averaged from three years of data collected from the 2004 through 2007 production seasons. Flower measurements and characteristics are from secondary flowers unless otherwise noted. Fruit characteristics and measurements are from secondary fruit unless otherwise noted. Foliage characteristics and measurements are from 3-foliate foliage unless otherwise noted.

Color terminology where noted follows the Munsell Book of Colors, Munsell Color, Baltimore, Md. (1976).

The following Tables 2–6 describe fruit, plant, foliage, flower and pest/disease characteristics of the new raspberry 'GRANDEUR' in comparison to the similar raspberry varieties 'PS-1040' (patented, U.S. Plant Pat. No. 10,142) and 'PS-1703' (patented, U.S. Plant Pat. No. 15,151).

TABLE 2

FRUIT CHARACTERISTICS

| Characteristic | 'GRANDEUR' | 'PS-1049' (US PP10,142) | 'PS-1703' (US PP15,151) |
|---|---|---|---|
| Color mature fruit | 5R 4/12 to 3/10 Light to medium red | 5R 3/6 to 3/8 Medium red | 5R 3/10 to 3/8 Medium red |
| Color achenes | 10YR 7/4 to 8/4 | 10YR 7/4 to 8/4 | 10YR 7/4 to 8/4 |
| Fruit Length (cm) | 2.2 | 1.9 | 1.9 |
| Fruit Width (cm) | 2.0 | 1.8 | 1.8 |
| Length/Width Ratio | 1.1 Slightly longer than broad | 1.1 Slightly longer than broad | 1.1 Slightly longer than broad |
| Seed weight (mg) | 1.4 | 1.2 | 1.4 |
| Druplets per berry | 93 | 100 | 85 |
| Fruit size | Large | Medium | Medium |
| Predominant shape | Conical | Conical | Conical |
| Evenness of color | Even | Even | Even |
| Glossiness | Medium | Medium | Strong |
| Adherence of recepticle | Weak | Weak | Weak |
| Firmness of flesh | Very firm | Very firm | Firm |
| Firmness of skin | Very firm | Very firm | Medium |
| Soluble Solids (% Brix) | 10.6 | 10.3 | 11.3 |
| Flavor | Very Good | Good | Excellent |

TABLE 3

PLANT CHARACTERISTICS

| Characteristic | 'GRANDEUR' | 'PS-1049' (US PP10,142) | 'PS-1703' US PP15,151) |
|---|---|---|---|
| General: | | | |
| Habit | Upright | Sem-upright | Semi-upright |
| Size | Medium | Medium | Medium |
| Productivity | High | Medium to high | High |
| Self fruitfulness | Yes | Yes | Yes |

TABLE 3-continued

PLANT CHARACTERISTICS

| Characteristic | 'GRANDEUR' | 'PS-1049' (US PP10,142) | 'PS-1703' US PP15,151) |
|---|---|---|---|
| Type of bearing | Everbearing | Everbearing | Everbearing |
| Primocane: | | | |
| Color | 10Y 7/4 to 7/6 Medium green-yellow | 5GY 7/4 to 6/4 Light green-yellow | 7.5GY 6/2 to 6/4 Medium to light green-yellow |
| Length (m) | 1.5 | 1.8 | 1.6 |
| Basal diameter (mm) | 17.8 | 15.1 | 15.8 |
| Diameter central ⅓ (mm) | 11.6 | 11.2 | 10.9 |
| Lateral length (cm) | 24.4 | 38.8 | 49.0 |
| No. fruiting laterals per cane | 20 | 14 | 17 |
| % of cane length fruiting | 31% | 30% | 46% |
| Internode length at central ⅓ (cm) | 5.4 | 6.1 | 6.2 |
| Anthrocyanin coloration | Medium | Weak to medium | Medium to strong |
| Pubescence | Absent | Absent | Absent |
| Length of vegatative bud | Medium | Medium to short | Medium to short |
| Strength of waxy coat | Ranges from absent to very weak | Strong | Ranges from medium to strong |
| Time of flowering | Medium | Medium | Early |
| Time of fruiting | Medium | Medium | Early |
| Length of fruiting season | Long | Long | Long |
| % of total yield | 43% | 49% | 54% |
| Flowering period | Late June to Late November | Late June to Late November | Early June to Late November |
| Harvest period | Late July to Late December | Late July to Late December | Early July to Late December |
| Primocane fruit weight (g) | 3.5 | 2.7 | 3.0 |
| Primocane yield (g/plant) | 1,979 | 1,711 | 2,228 |
| Young Shoots: | | | |
| Number | Medium | Medium | Medium |
| Anthocyanin coloration | Present | Present | Present |
| Anthocyanin intensity | Weak | Very weak to weak | Weak to medium |
| Thorns: | | | |
| Color | 7.5RP 3/6 Purple | 7.5RP 3/6 Purple | 7.5RP 3/6 Purple |
| Length central ⅓ (mm) | 1.6 | 2.3 | 1.9 |
| Presence on cane | Present | Present | Present |
| Density on cane | Medium | Medium | Medium to dense |
| Texture | Rigid | Rigid | Rigid |
| Attitude of the tip | Horizontal | Horizontal | Horizontal |
| Floricane: | | | |
| Color | 10YR 4/8 to 5/8 Brown | 5YR 4/4 to 4/6 Brown | 7.5YR 4/6 to 4/8 Brown |
| Length (m) | 1.1 | 1.3 | 1.2 |
| Length vegetative bud | Medium | Medium to short | Medium to short |

TABLE 3-continued

PLANT CHARACTERISTICS

| Characteristic | 'GRANDEUR' | 'PS-1049' (US PP10,142) | 'PS-1703' US PP15,151) |
|---|---|---|---|
| Strength of waxy coat (glaucosity) | Ranges from absent to very weak | Strong | Ranges from medium to strong |
| Fruiting lateral attitude | Erect to semi-erect | Erect to semi-erect | Horizontal to drooping |
| Time bud burst | Medium | Medium | Medium |
| Time of flowering | Medium | Medium | Medium |
| Time of fruiting | Medium | Medium | Medium |
| Length of fruiting season | Medium to long | Medium to long | Medium to long |
| % of total yield | 57% | 51% | 46% |
| Flowering period | Late April to Late June | Late April to Late June | Med April to Late June |
| Harvest period | Late May to Late July | Late May to Late July | Early May to Late July |
| Floricane fruit weight (g) | 3.6 | 2.5 | 2.7 |
| Floricane yield (g/plant) | 2,832 | 1,955 | 2,012 |

TABLE 4

FOLIAGE CHARACTERISTICS

| Characteristic | 'GRANDEUR' (3 Foliate) | 'PS-1049' (US PP10,142) (3 Foliate) | 'PS-1703' (US PP15,151) (5 Foliate) |
|---|---|---|---|
| General: | | | |
| Color of upper surface | 7.5GY 3/4 to 3/6 Medium green | 7.5GY 3/4 to 4/4 Medium green-yellow | 7.5GY 2/4 to 3/4 Medium to dark green |
| Color of lower surface | 5GY 6/2 to 7/2 Light to pale grey-green | 5GY 5/4 to 6/4 Pale yellow-green | 5GY 6/2 to 7/2 Light to pale grey-green |
| Shape in cross section | Ranges from flat to slightly convex | Slightly concave | Ranges from slightly concave to slightly convex |
| Arrangement | Compound | Compound | Compound |
| Relief between veins | Very strong | Medium | Medium to strong |
| Glossiness | Weak | Weak | Medium |
| Number of leaflets/leaf | Always 3 | Equal 3-5 | Mostly 5 |
| Terminal Leaflet: | | | |
| Length (cm) | 12.7 | 11.7 | 10.4 |
| Width (cm) | 9.1 | 9.2 | 5.5 |
| Length/Width Ratio | 1.4 Longer than broad | 1.3 Longer than broad | 1.9 Much longer than broad |
| Size | Medium to large | Medium to large | Medium to small |
| Shape | Cordate | Cordate | Lobed oblique |
| Shape of base | Cordate | Cordate | Acute |
| Shape of tip | Acuminate | Acuminate | Acuminate |
| Margins | Biserrate | Biserrate | Biserrate |
| Lateral Leaflet: | | | |
| Length (cm) | 10.5 | 10.4 | 9.2 |
| Width (cm) | 6.5 | 6.3 | 5.2 |
| Rachis length (cm) | 3.6 | 3.2 | 2.9 |
| Orientation | Opposite | Opposite | Opposite |
| Arrangement | Compound | Compound | Compound |
| Shape | Ovate | Ovate | Oblique |

TABLE 4-continued

| FOLIAGE CHARACTERISTICS | | | |
|---|---|---|---|
| Characteristic | 'GRANDEUR' (3 Foliate) | 'PS-1049' (US PP10,142) (3 Foliate) | 'PS-1703' (US PP15,151) (5 Foliate) |
| Overlapping | Touching | Touching | Free |
| Shape of the base | Oblique rounded | Oblique rounded | Acute oblique |
| Shape of the tip | Acuminate | Acuminate | Acuminate |
| Margins | Biserrate | Biserrate | Biserrate |
| Petiole: | | | |
| Length (cm) | 5.2 | 4.3 | 4.4 |
| Width (mm) | 3.0 | 2.6 | 2.9 |
| Thorn presence | Yes | Yes | Yes |
| Thorn orientation | Erect | Erect | Erect |
| Anthocyanin coloration of upper surface | Medium absent | Ranges from to very weak | Ranges from medium to strong |
| Pigmentation of lower surface | Light green-yellow | Light green-yellow | Light green-yellow |
| Stipule length (cm) | 0.9 | 1.1 | 0.9 |
| Stipule orientation | Erect | Erect | Erect |

TABLE 5

| FLOWER CHARACTERISTICS | | | |
|---|---|---|---|
| Characteristic | 'GRANDEUR' | 'PS-1049' (US PP10,142) | 'PS-1703' (US PP15,151) |
| Petal color | N 9.5/90% R to N 9.25/84.2% R White | N 9.5/90% R to N 9.25/84.2% R White | N 9.5/90% R to N 9.25/84.2% R White |
| Flower diameter (cm) | 2.4 | 2.1 | 1.9 |
| Petal length (mm) | 6.9 | 5.9 | 6.2 |

TABLE 5-continued

| FLOWER CHARACTERISTICS | | | |
|---|---|---|---|
| Characteristic | 'GRANDEUR' | 'PS-1049' (US PP10,142) | 'PS-1703' (US PP15,151) |
| Petal width (mm) | 3.1 | 3.0 | 3.0 |
| Petal length/ width ratio | 2.2 Much longer than broad | 2.0 Much longer than broad | 2.1 Much longer than broad |
| No. petals/ flower | 5.1 | 5.0 | 5.2 |
| No. sepals/ flower | 5.1 | 5.0 | 5.3 |
| Pedicel no. spines | Many | many | Medium |
| Peduncle anthocyanin presence | Present | Present | Present |
| Peduncle anthocyanin intensity | Very weak | Very weak | Weak |

TABLE 6

| PEST AND DISEASE REACTIONS | | | |
|---|---|---|---|
| Characteristic | 'GRANDEUR' | 'PS-1049' (US PP10,142) | 'PS-1703' (US PP15,151) |
| Two spotted spider mite | Susceptible | Susceptible | Susceptible |
| Grey fruit mold | Susceptible | Susceptible | Susceptible |
| Powdery mildew | Moderately Susceptible | Moderately Susceptible | Moderately Susceptible |
| Yellow rust | Moderately Susceptible | Moderately Susceptible | Moderately Resistant |

We claim:

1. A new and distinct variety of raspberry plant named 'GRANDEUR', as herein described and illustrated by the characteristics set forth above.

* * * * *